Figure 1:
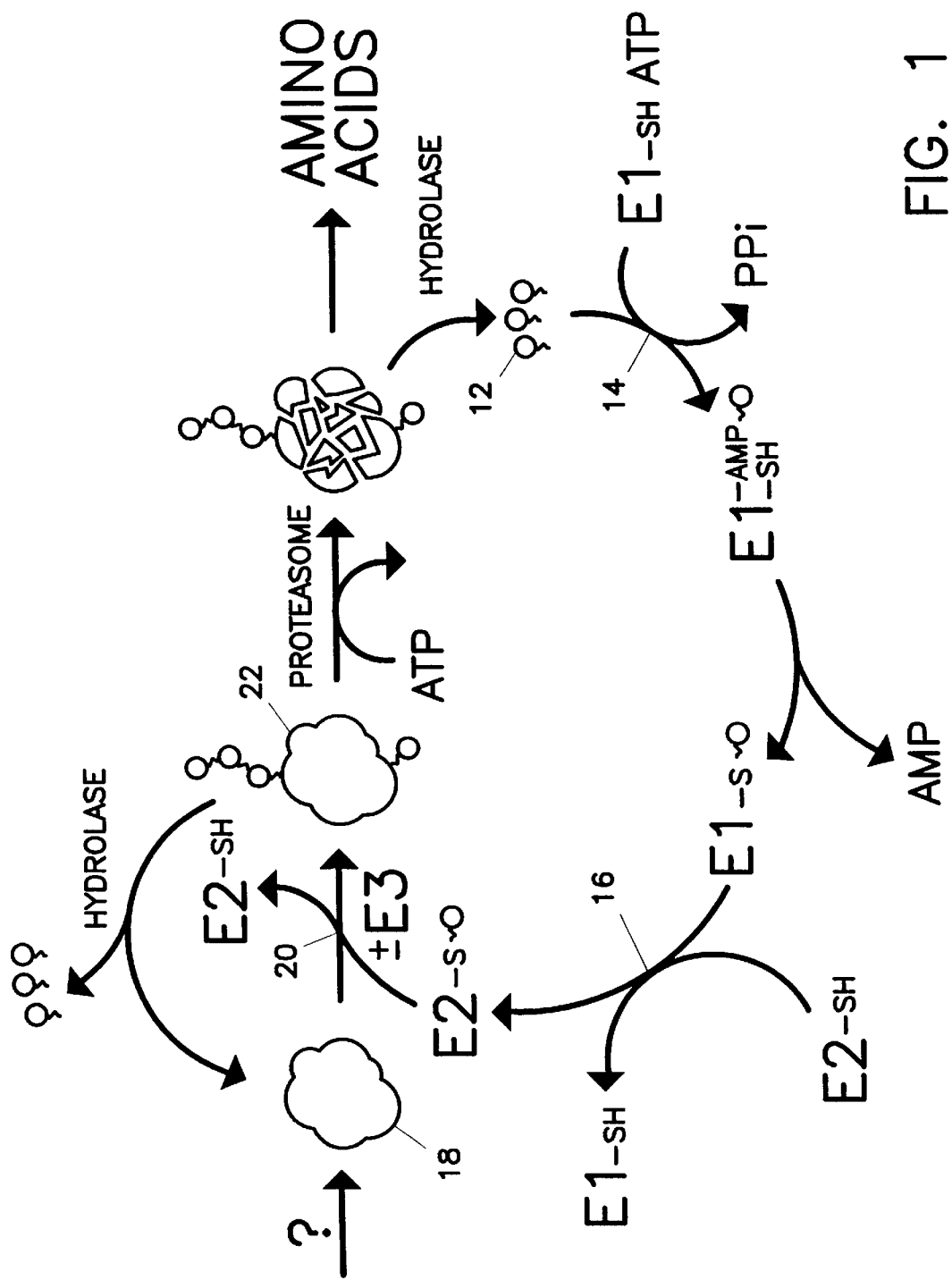

United States Patent [19]
Vierstra et al.

[11] Patent Number: 5,851,791
[45] Date of Patent: Dec. 22, 1998

[54] UBIQUITIN CONJUGATING ENZYME (E2) FUSION PROTEINS

[75] Inventors: Richard David Vierstra; Mark Mattnew Gosink, both of Madison, Wis.

[73] Assignee: Wisconsin Alumni Research Foundation, Madison, Wis.

[21] Appl. No.: 533,298

[22] Filed: Sep. 25, 1995

Related U.S. Application Data

[63] Continuation of Ser. No. 70,157, May 28, 1993, abandoned.

[51] Int. Cl.$^6$ .......................... C12P 21/06; C12P 21/04; C12N 9/10; C07H 21/04
[52] U.S. Cl. .................. 435/168.1; 435/69.7; 435/181; 435/188; 435/193; 536/23.2; 536/23.4; 536/23.5; 536/23.51; 536/23.53
[58] Field of Search ................................ 435/69.7, 172.3, 435/181, 188, 193, 68.1; 536/23.2, 23.4, 23.5, 23.51, 23.63, 23.13, 24.1, 24.2

[56] References Cited

PUBLICATIONS

Beidler, C.B., et al., "Cloning and High Level Expression of a Chimeric Antibody with Specificity for Human Carcinoembryonic Antigen," *J. Immunology*, 141:4053–4060 (1988).

Dreynck, R., et al., "Human Transferring Growth Factor–a: Precursor Structure and Expression in *E. coli*," *Cell*, 38:287–297 (1984).

Evans, G.I., et al., "Isolation of Monoclonal Antibodies Specific for Human c–mycf Proto–Oncogene Product," *Mol. Cell. Biology*, 5:3610–3616 (1985).

Hershko, A., and A. Ciechanover, "The Ubiquitin System for Protein Degradation," *Ann. Rev. Biochem.*, 61:761–807 (1992).

Hiatt, A., et al., "Production of Antibodies in Transgenic Plants," *Nature*, 342:76–78 (1989).

Hondred, D., and R. D. Vierstra, "Novel Applications of the Ubiquitin–Dependent Proteolytic Pathway Genetic Engineering," *Current Opinion in Biotechnology*, 3:147–151 (1992).

Shuttleworth, H.L., et al., "Nucleotide Sequence Analysis of the Gene for Protein A from *Staphylococcus aureus* Cowan 1 (NCTC8530) and Its Enhanced Expression in *Escherichia coli*," *Gene*, 58: 283–295 (1987).

Sullivan, M.L., and R.D. Vierstra, "A Ubiquitin Carrier Protein from Wheat Germ Is Structurally and Functionally Similar to the Yeast DNA Repair Enzyme Encoded by RAD6," *Proc. Natl. Acad. Sci. USA*, 86:9861–9865 (1989).

Sullivan, M.L., and R. D. Vierstra, "Cloning of a 16–kDa Ubiquitin Carrier Protein from Wheat and *Arabidopsis thaliana*: Identification of Functional Domains by In Vitro Mutagenesis," *J. Biol. Chem.*, 266:23878–23885 (1991).

Van Wezenbeek, P., et al., "Nucleotide Sequence of the Filamentous Bacteriophage M13 DNA Genome: Comparison with Phage fd," *Gene*, 11: 129–148 (1980).

Vierstra, R.D., "Protein Degradation in Plants," *Ann. Rev. Plant Physiol., Plant Mol. Biol.*, 44:385–410 (1993).

Watt, R., et al., "Nucleotide Sequence of Cloned cDNA of Human c–myc Oncogene," *Nature*, 303: 725–728 (1983).

*Primary Examiner*—Charles L. Patterson, Jr.
*Assistant Examiner*—Elizabeth Slobodyansky
*Attorney, Agent, or Firm*—Quarles & Brady

[57] ABSTRACT

A novel class of fusion proteins based on the ubiquitin-conjugating enzyme, or E2, is described. The fusion proteins include, in addition to the E2 activity, a protein binding ligand having a specific affinity for a target protein. It has been discovered that under cytosolic conditions, such E2 fusions will add a ubiquitin moiety to a target protein. Since ubiquitin addition triggers the endogenous cellular protein degradation pathway, such E2 fusion proteins can be used to selectively target proteins in a host for degradation. Thus, E2 fusion proteins genes can be introduced into transgenic organisms to defeat or inhibit natural activities or traits. The E2 fusion proteins can also be used by introduction into hosts for similar effects.

13 Claims, 7 Drawing Sheets

UBIQUITIN CONJUGATING ENZYME (E2) FUSION PROTEINS

This is a continuation of application Ser. No. 08/070,157 filed May 28, 1993 now abandoned.

FIELD OF THE INVENTION

The present invention relates to the field of molecular biology in general and relates, in particular, to a method for creating synthetic nucleotide sequences and resulting fusion proteins which are capable of adding ubiquitin to selected target proteins and invoking the ubiquitin-directed proteolytic process.

BACKGROUND OF THE INVENTION

Living cells are constantly manufacturing proteins for metabolic as well as structural purposes within the cell. The proteins are manufactured from individual amino acids present in the cytoplasm of the cell. At the same time, each individual cell is constantly degrading excess proteins that are either present in unwanted amounts or which are no longer needed at the current stage of the cell's development. In general, proteins are constantly being degraded into the individual amino acids, which are then reconstituted separately into different proteins useful for current cellular needs.

While the mechanisms for protein synthesis are widely understood and studied, the mechanisms for protein degradation are not so well characterized. One system in which a significant amount of information has been developed is the ubiquitin-directed proteolytic pathway. This system is illustrated in FIG. 1 and will briefly be described here.

Referring again to FIG. 1, beginning on the right hand side, and indicated at 12, are a plurality of ubiquitin proteins. Ubiquitin is a highly conserved 76-amino acid protein found in all eukaryotes. The ubiquitin sequence is so tightly conserved that there are only three amino acids which are varied amongst all plant and animal ubiquitin proteins yet studied. The actual three dimensional shape of the native ubiquitin molecule thus resembles the shape illustrated in FIG. 1, i.e., a ball with a string or tail, composed of the carboxyl terminal 5 amino acids, is attached thereto. In the ubiquitin-directed metabolic pathway, ubiquitin is covalently attached to proteins to be degraded to "tag" them for proteolysis. This process begins when free ubiquitin in the cell associates with a protein known as the E1 or ubiquitin activating enzyme. AMP is attached to the carboxyl terminus of the ubiquitin protein in an energy consumptive reaction and then, as indicated at 14, the carboxyl terminus of ubiquitin is attached through a thiol ester linkage to a cysteine group on the E1 molecule. Then a second enzymatic protein associated with the cascade, E2, also known both as ubiquitin conjugating enzyme (UBC) or ubiquitin carrier protein, interacts with the E1 molecule and the ubiquitin moiety is transferred from the E1 protein to the E2 protein, where it is again attached through a thiol ester linkage to a unique cysteine within the E2. This reaction is indicated at 16.

Eukaryotic cells have a significant number of different E2 proteins. Each of the E2s has a core region or body portion and the core regions of the various E2s are highly conserved. Many of the E2 proteins also contain a carboxyl terminus tail portion, and there is a high degree of sequence variation among the tail portions of the E2 proteins. In the plant *Arabidopsis thaliana*, at least 15 distinct E2 proteins have been identified and there may be 30 or more. It appears that each of the isoforms of E2's are specific to specific classes of proteins. For example, one particular E2 is known to have specificity for histones. Some E2s bind specifically to free ubiquitin. Some E2s are capable of acting independently, while others require an additional enzyme, referred to as an E3, or ubiquitin-protein ligase, in order to perform their function.

The function of the E2 molecules, or the ubiquitin conjugating enzymes, is to recognize and tag proteins which will be marked for degradation. The E2 molecules perform this tag by interacting, through a mechanism not yet fully understood, with the targeted protein to be degraded, and by covalently bonding the ubiquitin protein to the protein to be degraded. In FIG. 1, in the left center thereof, and indicated at 18, is the target protein. In the reaction indicated at 20, the E2 transfers the ubiquitin moiety to a lysine residue within the target protein. The target protein is illustrated again in the center of the figure with several ubiquitins attached. In cells in vivo, many repeats of ubiquitin are similarly added to the protein to be degraded. This can occur either because a chain of ubiquitins is added in one step to the protein to be degraded or it can occur where a single ubiquitin is added to the protein to be degraded, after which the chain of ubiquitins are added in sequence to that ubiquitin. Some proteins with only a single ubiquitin attached may survive in an altered form, but the research to date indicates that all proteins tagged with a multi-ubiquitin tag are degraded promptly.

In any event, proteins which have the ubiquitin repeat units attached to them are recognized by a particle existing in vivo in eukaryotic cells known as a proteasome, indicated at 22 in FIG. 1. The proteasome is a complex of proteolytic enzymes which recognizes proteins by the ubiquitin "tag" and which then proceeds to quickly and efficiently degrade the marked protein into its constituent amino acids. In this same process, the ubiquitin is released from the protein and is recycled. The amino acids thus produced are released into the cytoplasm.

No presently existing tool of molecular biology permits the targeted degradation of native proteins expressed in living organisms. The closest tool of molecular biology analogous to this technique is the evolving technology of antisense. In antisense technology, a gene is introduced into a living cell which is designed to produce an antisense RNA transcript. The antisense RNA transcript is intended to hybridize under in vivo conditions with an mRNA transcript natively present in the cells. The hybridization of those two RNA molecules creates a double stranded complex which is then degraded by yet uncharacterized cellular mechanisms. The net result is that the level of expression of the gene creating the target RNA is dramatically reduced or, in some cases, practically eliminated. It has also been proposed that free antisense RNA molecules might be delivered into the blood stream of vertebrates in order to suppress the expression of unwanted proteins.

There are no known prior attempts to use the ubiquitin protein degradation pathway to artificially induce ubiquitination and degradation of targeted proteins.

SUMMARY OF THE INVENTION

The present invention is summarized in that synthetic E2 molecules are created which include a body portion, a tail portion which is either natural or synthetic, and a heterologous protein binding ligand attached to the carboxyl end of the tail portion. It has been demonstrated that such molecules are capable of adding a ubiquitin particle to target proteins recognized by the protein binding ligand.

It is a further object of the present invention to describe gene sequences which are capable of causing the expression of such synthetic E2 protein recognition molecules in heterologous hosts.

It is also a feature of the present invention in that indigenous proteins in transgenic organisms can be targeted for degradation through the use of such synthetic E2 protein recognition molecules.

Other objects, advantages, and features of the present invention will become apparent from the following specification when taken in conjunction with the accompanying drawings and sequence listings.

BRIEF DESCRIPTION OF THE DRAWINGS

FIG. 1 is a schematic illustration of the ubiquitin-directed protein degradation cycle as it occurs in eukaryotic cells.

FIG. 2 is a schematic illustration of a prototype molecule constructed in accordance with the present invention.

FIG. 3 is a schematic illustration of a synthetic molecule constructed of UBC4 and a c-myc ligand, and its use to tag a target antibody molecule with ubiquitin.

FIG. 4 is a schematic illustration of a molecule composed of UBC4 and TGFα protein, and its use in directing ubiquitin addition to a target protein.

FIG. 5 is a schematic illustration of a molecule composed of UBC4 and gene V, and its use in directing ubiquitin addition to a target protein.

FIG. 6 is an illustration of a molecule composed of UBC4 and protein A and its use in directing ubiquitin addition to a target protein.

FIG. 7 is a schematic illustration of a proposed molecule consisting of UBC4 and an antibody, and its use in directing ubiquitin attachment to a protein.

DESCRIPTION OF THE PREFERRED EMBODIMENT

It is proposed, in accordance with the present invention, that a novel class of E2 derived fusion proteins be constructed. This novel class of E2 fusion proteins is illustrated, as a prototype, in FIG. 2. This class of E2 proteins, are constructed so as to add a ubiquitin moiety with specificity to a target protein, and are composed of three main constituents as illustrated in FIG. 2. One constituent, designated at 24, is a natural or artificial E2 protein core region. The second element, indicated at 26, is a spacer which can be either an artificially constructed spacer or a tail region from a native E2 isoform. The third constituent, designated at 28 in FIG. 2, is a protein binding ligand, again either natural or artificial, which has unique specificity to a target protein of interest.

The function of the E2 fusion protein molecule described above, is to add one or more ubiquitin residues to a target protein of interest, such a protein being indicated at 30 in FIG. 2. Since the pathway of ubiquitin-directed protein degradation in vivo in cells is actuated by the addition of ubiquitin to proteins to be degraded, all indications are that the addition of such ubiquitin protein tags to specific proteins will cause their degradation. In this manner, it becomes possible to target specific proteins for degradation through the use of novel E2 proteins such as those described above.

As also described briefly above, each of the class of proteins called ubiquitin conjugating enzymes, or E2s, consists of one or both of two main constituent domains. All known E2 isoforms include a core region, which is usually approximately 150 amino acids in length. The core region includes within it a unique cysteine residue, which is necessary for the formation of the ubiquitin-E2 thiol ester intermediate necessary for the cycle illustrated in FIG. 1. It is not clear that the cysteine must be unique. The core region of various E2s may include an amino terminus with a region containing hydroxylated and uncharged residues, which are associated with increasing the rate of thiol ester formation. Described below in SEQ ID NOS: 1 and 3 are the coding regions for two different E2s isolated from two different plant species. The two sequences encode proteins (SEQ ID NOS: 2 and 4) which contain similar, though not identical, core regions. These two sequences are exemplary, and several other E2 core region sequences have been sequenced and published. What is required of the E2 core region is that it be capable of functioning so as to participate with an E1 protein linked to a ubiquitin in a transesterification process to form the thiol-ester linkage of the E2 core region to the ubiquitin. The E2 core region must also be capable of transferring the ubiquitin to the target protein in the manner described in FIG. 2 and below. It is not believed that the source of origin of the E2 protein is of any criticality. Since ubiquitin proteins are extraordinarily highly conserved among all eukaryotes, and since the chemical interaction required in the procedures described here is between the E2 molecule and the ubiquitin, the core regions from E2 molecules from virtually all eukaryotic sources should be able equivalently well in vivo to bind to and transfer endogenous ubiquitin. As demonstrated below as well, plant-origin E2 core regions are capable of adding ubiquitin to animal or viral origin proteins and are capable of using either plant or animal origin ubiquitins. Hence, there appears to be little or no species, or even kingdom specificity, to the origin of the E2 domains. Similarly, any eukaryote which expresses a compatible ubiquitin is a target for this approach. All known eukaryotic ubiquitins fit this criteria, and hence it appears that E2s from any eukaryotic source may be used in conjunction with ubiquitins present in any target host.

There are differences between the two eukaryotic E2 isoforms which are used in the examples below. UBC1 is an E2 isolated from *Arabidopsis thaliana*, while UBC4 is an E2 isolated from wheat. The E2s UBC1 and UBC4 differ in both their specificity and their method of activity. The native UBC4 E2 is capable, in vitro, of binding to the target protein alone, without the need for an ubiquitin protein ligase, or E3, molecule. UBC4 strongly associates with histones, due to an interaction between the strongly acidic carboxyl terminus tail of UBC4 which interacts with the basic histone molecules. Therefore, UBC4 may be associated with histone degradation in its native system, although this is not proven. UBC1 requires the presence of the ubiquitin protein ligase, or E3, molecule in order to direct the ubiquitin addition to a target protein. In comparing the UBC1 and UBC4 molecules, the principal difference at a structural level lies in the fact that UBC4 possesses a tail region at the carboxyl terminus of its protein sequence, while UBC1 possesses no such tail. These two examples are illustrative of the difference between E3-dependent and E3-independent E2 isoforms. It has been previously reported by the investigators here that the transfer of a UBC4 tail from UBC4 to UBC1 confers on the UBC1 protein an affinity for histones. Hence, it has been postulated that the tail portion of E2 is responsible for the affinity to the protein which is to be signaled for degradation. Separately, it is now reported here that in the absence of a spacer region between the carboxyl terminus of a tail-less E2, such as UBC1, an E2 fusion protein strategy does not result in ubiquitin addition to the substrate protein.

Thus a tail-less E2 variant cannot be used in the process of the present invention without adding a native or artificial spacer or tail to its carboxyl terminus. Conversely, as described below, it has been found that the addition of a synthetic spacer region between the core region of an UBC1 type E2, and the protein-binding ligand, permits functional utilization of the UBC1 type E2 molecule in a function E2 fusion protein which operates independently of E3. Accordingly, it is a requirement of an effective E2 fusion protein molecule in accordance with the present invention that between the core region of the selected E2 and the protein-binding ligand that there be a spacer. A natural E2 tail may serve as the spacer, or an artificially constructed amino acid sequence will work additionally well as the spacer. It is also possible that the spacer can be added to or a part of the protein-binding ligand. For example, many single chain antibody sequences include rigid amino terminal domain that could serve as the spacer. It has been found that the spacer should optimally be at least four amino acids long, in order to permit both the proper functioning of the E2 core region and the proper binding and specificity of the protein-binding ligand for the substrate to which ubiquitin is to be added.

Figure 2:
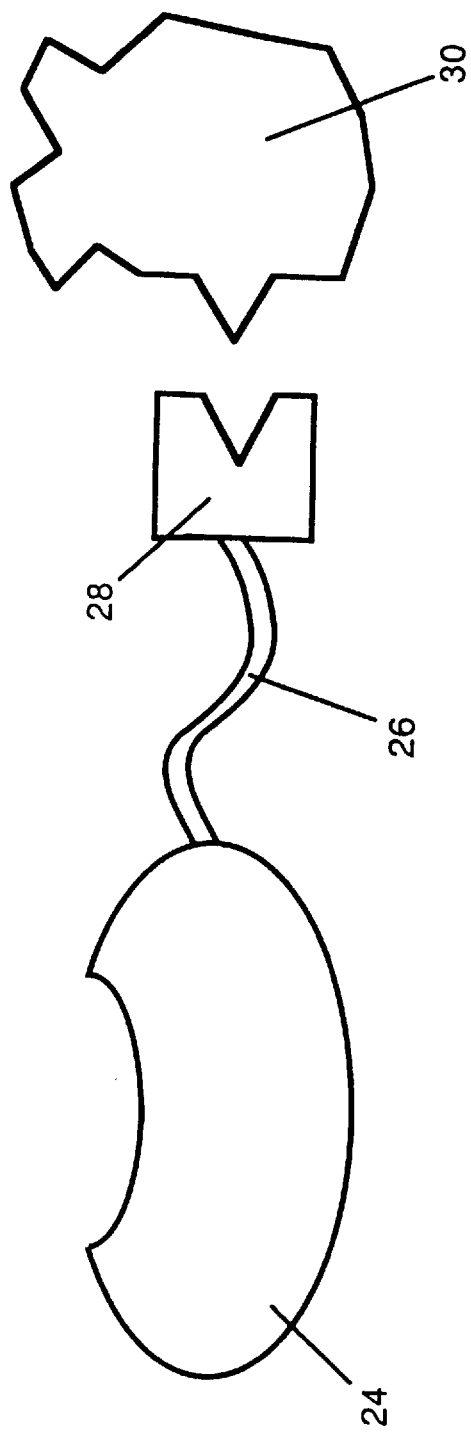

Also shown in FIG. 2 as a part of the E2 fusion protein is a protein-binding ligand 28, intended to have specific affinity for a targeted protein. The protein binding ligand can be any of a large number of possible amino acid sequences, as long as the encoded ligand provides specific binding to the target protein of interest. There are many examples of possible protein binding ligands. Protein science has generally become aware of the specific affinities between protein hormones, and the membrane bound receptor proteins with which they normally interact. It is therefore possible to use either one of these proteins, either the receptor or the hormone, as a protein binding ligand for the other. The responsible binding domain of either the hormone or the receptor may also be used, rather than the entire protein. It is possible, as described below, to use protein A as a ligand which binds specifically to antibodies. Also illustrated below is the use of a single protein which, in its native form, forms a dimer with other similar proteins in vivo, to target ubiquitin addition to the associated proteins in vivo. This demonstrates that native protein-to-protein associations may be used to identify protein-binding ligands. It is possible to use as the protein binding ligand an epitope which will be specifically bound by a particular antibody. In most situations, however, what will be ultimately desired for the protein binding ligand would be an antibody, or at least the recognition portion of an antibody, such as a single chain fragment antibody. For proteins which are not known to have another protein having specific attraction for them, the ability to create and utilize antibodies recognition domains specific for the target protein is essential. Through the use of antibody recognition sequences for the protein binding ligand, it is possible to target virtually any protein in a biological system for ubiquitin addition, and ubiquitin-directed protein degradation, in the manner described herein using an E2 fusion protein. All that seems to be required is for the target protein to have at least one lysine residue to which the ubiquitin may be attached.

It is possible to produce the E2 fusion protein of FIG. 2 by a variety of processes for use in ubiquitin-directed protein degradation. For example, it is possible to clone and/or construct a DNA sequence which, in its entirety, codes for an E2 fusion molecule of the class shown in FIG. 2. The DNA coding sequence could include, working 5' to 3', first the coding sequence for a selected E2 core region, such as those native sequences described in the sequences below, or could include a consensus or artificial E2 core region sequence. The DNA coding sequence would then include 3' to the core region sequence, a sequence encoding a spacer, or a tail region from E2. Again, this portion could be native or artificial, and both the core region and spacer could be from a single native E2, as in the case of UBC4 below. Finally, at its 3' end, the coding sequence would include the coding region for the protein binding ligand. When such a coding region for an E2 fusion protein is placed behind a promoter effective in a host of choice, and 5' to a transcription terminator, an expression cassette for the recombinant sequence expressing an E2 fusion protein, such as illustrated in FIG. 2, is created. That expression cassette can then be transformed into a heterologous host and expressed. Various transformation techniques for plants and animals are known in the art and need not be described further here. The E2 fusion protein thus expressed will then direct ubiquitin addition to a target protein of interest in vivo. This ubiquitin tagging will direct degradation by the cell, using its normal processes, of the target protein. In this way, transgenic organisms can be created which differ from their native or non-transformed ancestors by the active degradation of a specific unwanted protein. In this way it is possible to "turn off" proteins which are not desired to be expressed. This approach can be used in animal, plant, microbial or fungal systems which have an active ubiquitin-directed proteolytic pathway, to turn off unwanted activities, structures, traits or activities.

Alternatively, E2 fusion proteins such as those described and illustrated in FIG. 2 can be produced by expression in one host for ultimate delivery into another. For example, it is possible to take a synthetic coding sequence, as described in the preceding paragraph, and express that sequence in a prokaryotic host to produce E2 fusion protein, assuming only that the promoter is properly chosen. For example, it is quite common to produce therapeutic proteins by the fermentation of prokaryotic bacteria, and then to, subsequently isolate and purify the desired protein. In this fashion, useful quantities of E2 fusion proteins can be produced and isolated. The protein can then be delivered to an organism for possible therapeutic or other treatment. If production of the E2 fusion protein is performed outside of the host, it is envisioned that further treatment or modification of the E2 fusion protein may be desired. For example, liposome encapsulation of E2 fusion proteins may aid in their introduction into target cells. Alternatively, further protein domains could be added to the amino terminus of the E2 fusion proteins to target cellular receptors to induce introduction of the proteins into targeted cells in vivo.

A wide variety of possible applications for this technology are envisioned. In plant systems, it becomes possible to target the degradation of a specific enzyme, to turn off an unwanted plant metabolic pathway. For example, it now becomes possible to alter the secondary metabolite products of a plant by targeting for degradation one or more enzymes in the cascade for the unwanted secondary metabolite. The E2 fusion protein approach offers the promise of another mechanism for the control of virus infection in plants, by targeting the degradation of either the viral coat protein or one or more viral enzymes, e.g. a transcriptase, necessary for viral replication or activity in infected plant cells. It also becomes possible to target the degradation of specific cellular receptors, to diminish sensitivity to one or more otherwise undesirable effects caused by exposure to some environmental stimulus. It is possible to target the degradation of specific plant phytochromes enzymes, so as to alter plant vigor and growth.

In mammalian systems, analogous applications for this technology are also envisioned. Again, attempts can be made to interfere with viral pathogenicity by targeting for degradation either viral coat protein or enzymes necessary for viral replication or infection. It is possible to target for the degradation of onco-proteins, as a possible therapeutic strategy to try to slow or alter the process of oncogenesis. It is possible to target for degradation unwanted growth factors, or factors associated with the processes which are desired to be hindered for some period of time, such as blood clot formation. In general, it is envisioned that this technology offers the ability generally to target specific endogenous proteins for degradation, and to thus inhibit the otherwise native expression of proteins. In this manner, this technology provides an alternative to the "antisense" technology as a mechanism for interfering with native cellular processes in a quite specific manner.

This approach does have one significant advantage over the "antisense" approach. Antisense requires RNA-level sequence identity to be effective and, hence, for an activity caused by several isozymes, each isozyme must be separately targeted. The approach here could be used to target an active domain to direct degradation of all proteins with the domain. Hence protein families can be targeted with a single E2 fusion protein as well as specific proteins.

EXAMPLES

1. Common Methods and Materials

A. Materials

Oligonucleotides were synthesized as described in the sequences listings below, and were provided by E. I. du Pont. Restriction enzymes, M13mp18 single stranded DNA, and T4 polynucleotide kinase were purchased from New England Biolabs. VCS-M13 was purchased from Stratagene. Shrimp alkaline phosphatase (SAP) was purchased from United States Biochemical. Taq DNA polymerase was purchased from Perkin Elmer Cetus. E1 protein was synthesized in *E. coli* utilizing the TaUBA1 gene as described in Hatfield and Vierstra. *J. Biol. Chem.,* 265:15813–15817 (1992), and was then purified by the method described in Ciechanover et al., *J. Biol. Chem.,* 257:2537–2542 (1982). Human ubiquitin was used and was purified by the method of Haas and Wilkinson, *Biochem. Prep.,* 15:49–60 (1985), and was then radiolabeled with carrier-free $Na^{125}I$ by the chloramine-T method as described by Ciechanover et al., *Proc. Natl. Acad. Sci USA,* 77:1365–1368 (1980). Rabbit reticulocyte extract (untreated) was purchased from Promega Corporation. The wheat germ extract was prepared according to the method of Hatfield and Vierstra, *Biochem.* 28:735–743 (1389). Anti-(c-myc) monoclonal-antibodies derived from clone 9E10, and the c-myc peptide, were purchased separately from Oncogene Science, Inc. Alkaline phosphatase-conjugated goat anti-mouse immunoglobulins were purchased from Kirkegaard and Perry Laboratories Inc. Human epidermal cell membranes containing the epidermal growth factor receptor (EGFR) and purified epidermal growth factor (EGF) were a gift. The cDNA copy of the transforming growth factor α (TGFα) gene was a personal gift, but is described in Derrick et al., *Cell,* 38:287–297 (1984). Monoclonal antibody against the ribosomal protein S3 was a gift. All other reagents were purchased from Sigma.

Chromosomal DNA from *Staphylococcus aureus* was purified as described for *E. coli* by Perbal, *A Practical Guide to Molecular Clonings* (1984). *E. coli* cell extracts infected with M13 were prepared by inoculating LB media, containing tetracycline at 12 μg/ml, with 1/100th volume of an over-night culture of the *E. coli* strain of XL1-Blue. The culture was incubated with vigorous shaking for 1 hour at 37° C. and infected with VCS-M13 (Stratagene) at a multiplicity of infection of 10. Infected cells were incubated for an additional 1 hour, after which kanamycin was added to 100 μg/ml, and the culture was incubated for an additional 6 hours. The cells were harvested and lysed as described for the *E. coli* cultures following induction in Sullivan and Vierstra, *J. Bio. Chem.,* 266:23878–23885 (1991). The M13-uninfected cell extracts were prepared as described above except that M13 phage and kanamycin were omitted.

B. Construction of UBC1 and UBC4 Expression Vector Cassettes.

Unless stated otherwise, all techniques were performed according to the protocols as described by Sambrook et al., *Molecular Cloning: A Laboratory Manual,* 2nd Ed., Vols. 1–3 (1989). Creation of the expected site-directed versions and insertion of the various DNA fragments described below in their proper orientation were confirmed by subsequent sequence analysis. All studies began with the cDNA copies of the UBC4 gene from wheat (*Triticum vulgare*) as described in Sullivan and Vierstra, *J. Biol. Chem.* 266:35:23878–23885 (1991), and the UBC1 gene from *Arabidopsis thaliana* from Sullivan and Vierstra, 1991, supra, contained within the phagemid, pUC118 or pBluescript from Stratagene, respectively. A unique XhoI restriction endonuclease site was placed immediately upstream of the translation termination sites in both the UBC1 and UBC4 coding regions by site-directed mutagenesis performed as described by Kunkel et al., *Methods in Enzymol.,* 154:367–382 (1987). This site-directed mutagenesis was performed using the oligonucleotides RV155 and RV131 which are presented as SEQ ID NOS: 6 and 5 below respectively. The mutagenized UBC1 cDNA was then ligated into the pET 3a plasmid vector containing the UBC1 gene (Sullivan and Vierstra, 1991) as a SalI/BamHI cassette replacing the wild-type UBC1 gene. This replacement created an expression plasmid designated pET-UBC1. The mutagenized UBC4 cDNA was ligated into the pET 3a plasmid vector containing UBC4 (Sullivan and Vierstra, 1991) as a SphI/BamHI cassette replacing the wild-type UBC4 gene in that vector. This replacement created an expression plasmid designated pET-UBC4. Insertion of the XhoI site into UBC1 and UBC4 resulted in the addition of a dipeptide, Leu-Glu, to the carboxyl terminus of the native protein sequence of each protein as encoded by the respective DNA expression plasmids.

C. Synthesis of UBC1 and UBC4 Proteins With Carboxyl-Terminal Additions.

Additions to the carboxy-terminus of UBC1 and UBC4 proteins was accomplished by ligation of appropriate synthetic oligonucleotide pairs or double stranded DNA fragments into the XhoI site at the 3' end of the corresponding DNA coding sequences for the respective proteins. A phosphate group was first added to the 5'-end of the synthetic nucleotides using T4 polynucleotide kinase. Reactions containing the oligonucleotide at a final concentration of 6.67 μM, 400 μM ATP, and 0.33 units/μl of T4 polynucleotide kinase dissolved in T4 polynucleotide kinase buffer, and were incubated at 37° C. for 30 minutes. The complementary oligonucleotide pairs were annealed to each other through the addition of one-tenth volume of 10× Annealing Buffer (Biorad) and the mixture heated to 80° C. Reaction mixtures were then allowed to cool to room temperature over approximately 1.5 hours.

Prior to the insertion of the altered DNA coding sequences including carboxyl terminal additions into the expression plasmids, pET-UBC1 and pET-UBC4, the plasmids were digested with XhoI and treated with shrimp alkaline phosphatase (SAP) to reduce the frequency of self ligation. Dephosphorylation of XhoI-digested plasmids was performed using SAP according to the methodology described by the supplier. After dephosphorylation, the remaining enzyme was denatured by heating the entire reaction mixture to 70° C. and holding it for 10 minutes.

D. Construction of c-myc expression vectors.

This example was intended to demonstrate the use of an epitope as the protein binding ligand. The epitope chosen, because of convenient access to the monoclonal antibody, was from the c-myc protein. The oligonucleotide pair, designated RV138 and RV139, presented as SEQ ID NOS: 7 and 9 respectively below, are designed to form a double stranded DNA cassette that encodes a 10-amino-acid epitope SEQ ID NO: 8 recognized by the mouse monoclonal antibody designated clone 9E10. The mouse monoclonal antibody clone 9E10 was generated against the oncogene protein c-myc as described by Evan, et. al., *Mol. Cel. Biol.* 5:12:3610–3616 (1985), and the ten amino acid epitope for the anti-c-myc antibody is described in Koledziej and Young, *Methods Enzymol.* 194:508–519 (1991). The c-myc epitope cassette was ligated into the XhoI site of pET-UBC1 and pET-UBC4 to create two plasmids then designated pET-UBC1-(c-myc) and pET-UBC4-(c-myc). The presence of the c-myc epitope on the protein expressed on each of these plasmids was established by inducing expression of the E2 proteins made by these plasmids and then screening for c-myc positive strains by immunoblot analysis using the c-myc specific antibody. In this way, it was assured that the plasmids properly expressed the epitope recognized by that antibody.

E. Construction of a UBC1-spacer-(c-myc) expression vector.

Figure 3:
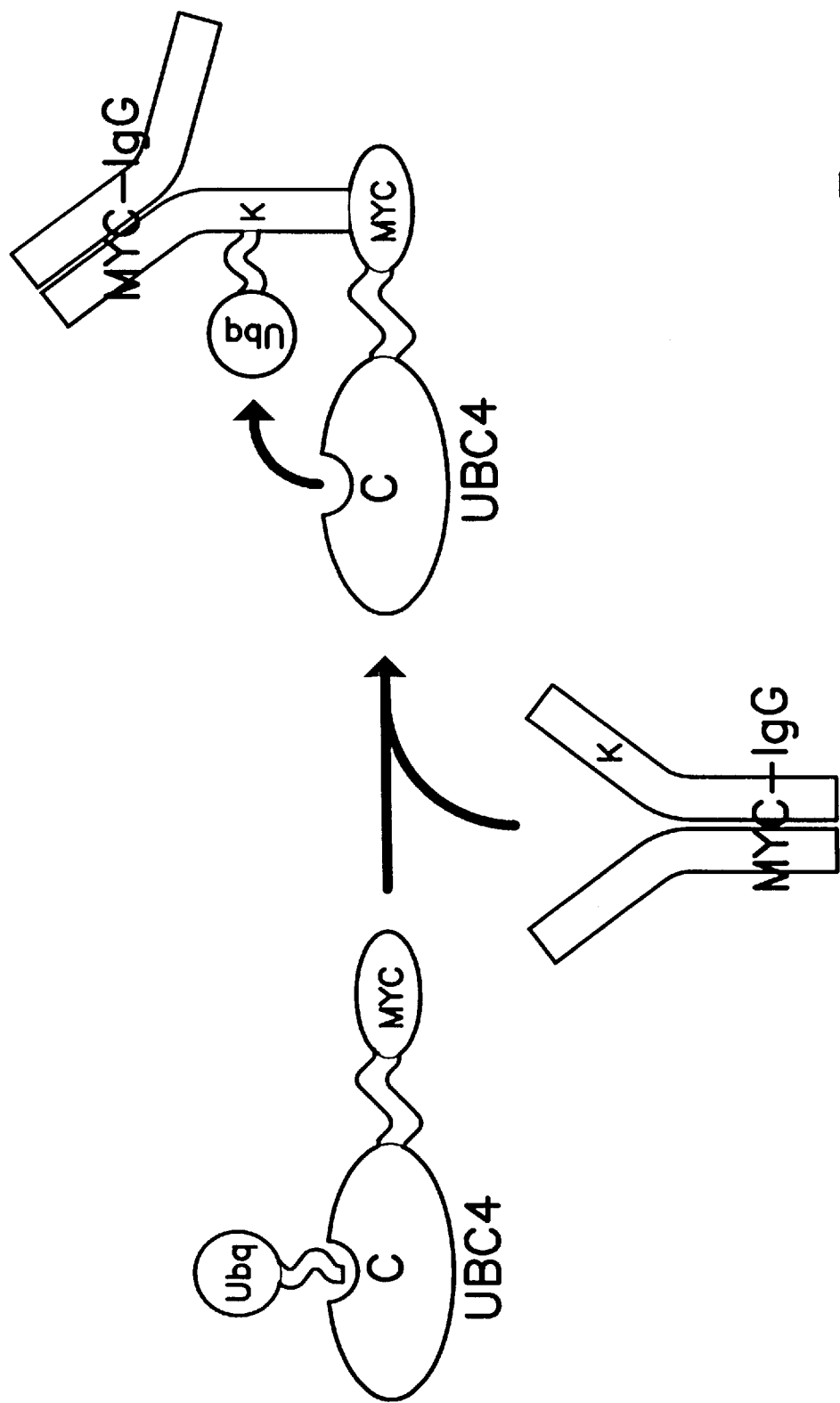

In addition to constructing a vector in which the c-myc epitope was ligated to the carboxyl terminus of the UBC1 E2 protein, it was also desired to add a spacer between the core region of the UBC1 E2 molecule and the protein-binding ligand, in this case the c-myc epitope. To do this, an oligonucleotide pair designated RV136 and RV137, set forth as SEQ ID NOS: 16 and 18 below, was designed. This oligonucleotide pair, when annealed and expressed in a host, is intended to create a 10 amino acid spacer consisting of the amino acids set forth in SEQ ID NO: 17. This cassette was further designed to ligate into XhoI site of pET-UBC1. Upon ligation of the spacer oligonucleotides, the original XhoI site in pET-UBC1 was lost and a new XhoI site was created at the 3-'end of the spacer cassette to allow for further insertions. After insertion of the spacer cassette, the c-myc cassette was then ligated into the XhoI site in the spacer of pET-UBC1-spacer, creating the new expression vector plasmid designated pET-UBC1-spacer-(c-myc). This construction was intended to demonstrate the sufficiency of an artificial spacer between the core protein of the E2 and the protein binding ligand. This construct, and its use is generally illustrated in FIG. 3.

F. Construction of a UBC4-TGFα expression vector.

To obtain a sequence for a TGFα coding region, it was decided to clone by PCR a DNA region encoding amino acid 41–89 of the human peptide hormone transforming growth factor α (TGFα). The activity of the TGFα hormone has been determined to result from its binding to a specific cellular receptor, known as the epidermal growth factor receptor (EGFR) present as a cellular receptor in many cells in a human body. The portion of the coding sequence for the TGFα gene (amino acid 41–89 of the native protein), includes the binding ligand which natively binds to the EGF receptor.

Figure 4:
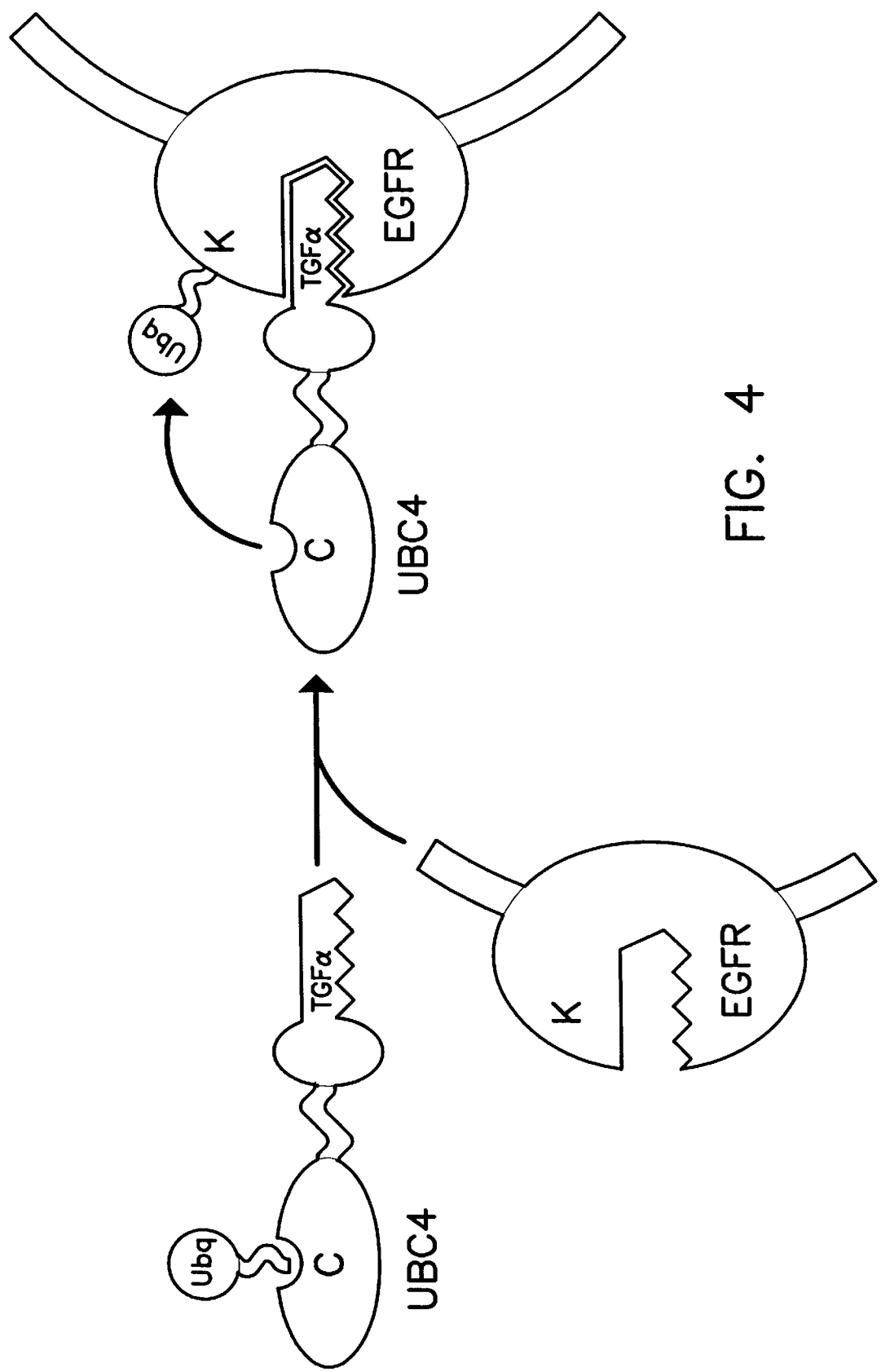

Shown as SEQ ID NOS: 10 and 11 below are a pair of oligonucleotides designated RV151 and RV154, which were designed to be primers for amplification of the desired coding region from TGFα by polymerase chain reaction (PCR). The PCR template consisted of a plasmid containing the cDNA copy of the TGFα pre-hormone form, the sequence of which can be found in GENEBANK accession #M31172. Additional DNA sequence was added to oligonucleotide RV151 to encode a XhoI site. The PCR was performed on the template to create multiple copies of a PCR product. The SalI site was then used to ligate the PCR product into the XhoI site of pET-UBC4 to create an in-frame coding region fusion between the coding region for UBC4 and TGFα. Likewise, oligonucleotide RV154 was designed to contain a stop codon at the 3'-end of the hormone coding region followed by a SalI site. The product of PCR amplification was digested with SalI and XhoI, and was then ligated into the XhoI site of pET-UBC4, to create an in-frame fusion of UBC4 and TGFα proteins while maintaining the XhoI site at the 5'-end thereof. This plasmid was designated pET-UBC4-TGFα). This fusion protein and its use is schematically illustrated in FIG. 4.

G. Construction of a UBC4-GENEV expression vector.

Figure 5:
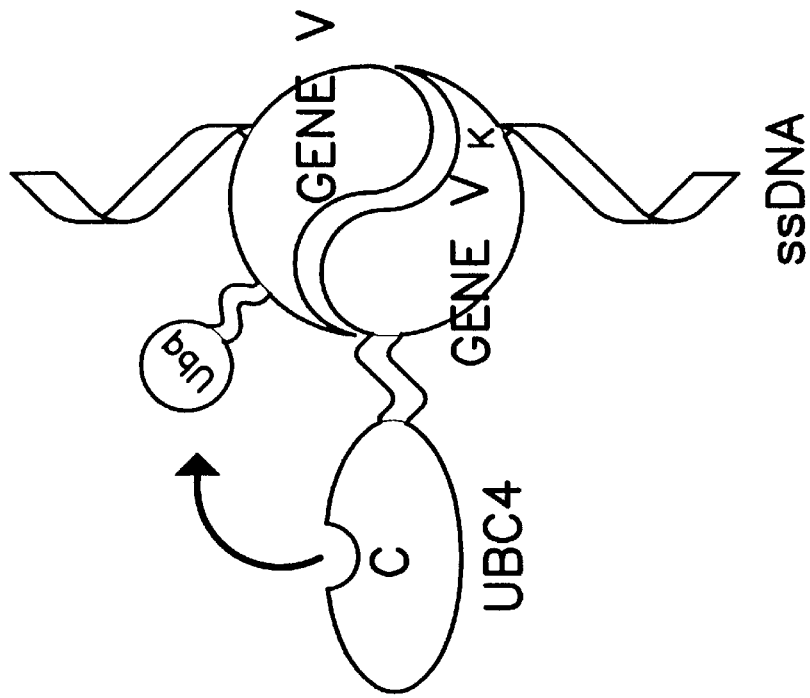
Figure 5:
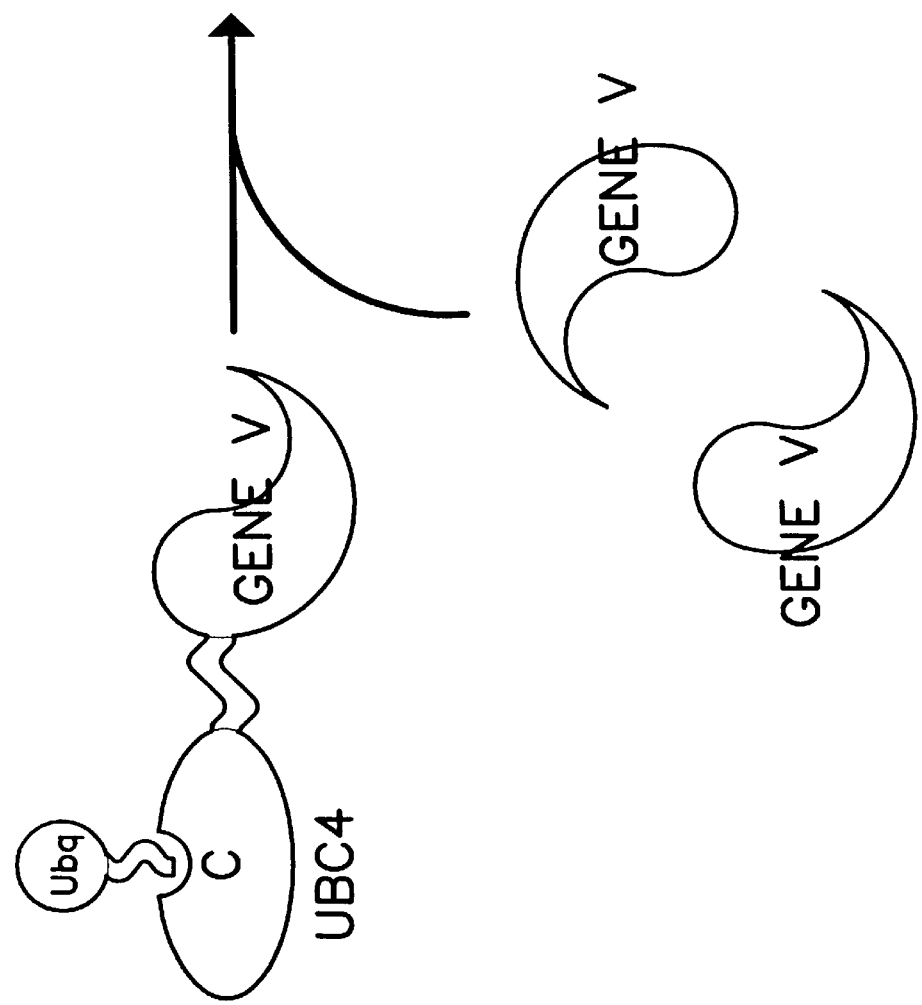

GeneV is a protein from the M13 phage. In its native form, the protein associates in homo-dimers. The intent of this expression was to test the ability of a single subunit of a dimer to serve as a protein binding ligand within the present invention. Again the protein coding sequence of interest was prepared by PCR reaction. The oligonucleotide pair, RV220 and RV221, SEQ ID NOS: 13 and 12 respectively, were designed to amplify by PCR the complete coding region of the GeneV protein from the bacteriophage M13, as set forth in GENEBANK accession #VB0018. The oligonucleotides also include unique XhoI and SalI sites such that the GeneV coding region amplified by PCR could be digested with XhoI and SalI and the resulting 271 base pair fragment then could be ligated into the XhoI site of PET-UBC4 and the same method described with the UBC-TGFα construct described above. Again this construct made, in a similar fashion, an in-frame fusion of the UBC4 protein with the GeneV protein domain, and the construction was designated PET-UBC4-GeneV. This construction and its use are schematically illustrated in FIG. 5.

H. Construction of a UBC4-Protein A expression vector.

Protein A from *Stapholoccus aureus* has a high natural affinity for many classes of antibodies. The antibody-binding region of Protein A binds to the Fc portion of antibodies rather than to the antigenic recognition site. This was used to test to see if antibodies could be targeted for destruction, although this test would be generic to antibodies and not specific to the epitope recognized by the antibodies. This example is also intended to demonstrate that classes of proteins can be targeted through the use of a domain for the protein binding ligand that recognizes classes of proteins.

Figure 6:
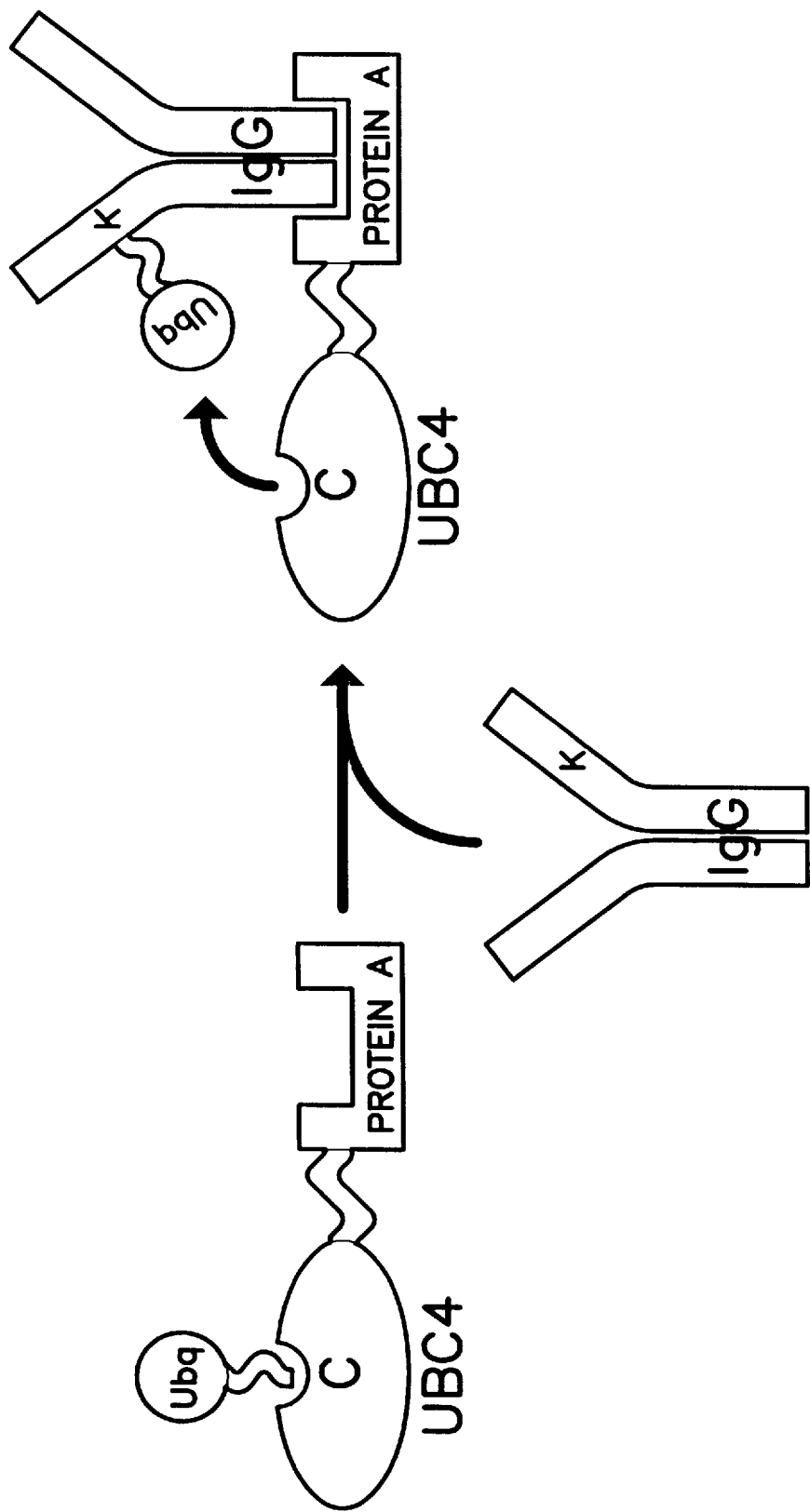

Again it was decided to amplify by PCR the coding region of the antibody-binding D domain (amino acids 90–193) of Protein A, as set forth in GENEBANK Accession #M18264. A pair of oligonucleotide primers, designated RV242 and RV238, set forth as SEQ ID NOS: 14 and 15 was designed to both amplify the PCR product and add the appropriately desired restriction sites at the end of the PCR product. The PCR process was performed on *S. aureus* chromosomal DNA. Again, the oligonucleotides provided for unique XhoI sites at each ends of oligonucleotide to allow the amplified fragment to be digested with XhoI, and then to be ligated into the XhoI site of pET-UBC4. This insertion created an in frame fusion of UBC4 protein with the Protein A D domain and the resulting plasmid was designated pET-UBC4-Protein A. The presence of antibody-binding domain in the expressed pET-UBC4-Protein A construct was demonstrated by expression in *E. coli* and immunoblot analysis using alkaline phosphatase-conjugated immunoglobulin G. The resulting fusion protein is schematically illustrated in FIG. 6.

2. Ubiquitin conjugation assays.

A. Expression and assay of the UBC1 and UBC4 constructs.

All pET3a expression plasmids containing the UBC1 and UBC4 expression cassettes were transformed into *E. coli* strain BL21(DE3). Following induction of pET3a expression cassette by the addition of isopropyl β-D-thiogalactopyranoside to logarithmic growth phase cultures, the cells were harvested and lysed as described in Sullivan and Vierstra, (1991) supra. All experiments were performed using crude lysates of cells containing the induced plasmids. Ubiquitin conjugation assays with theses lysates were performed as previously described in Sullivan and Vierstra, (1991) supra, except that the incubation time for all assays was 2 hours. Each of the reactions was formed in 20 μl total volume containing 1–4 μl of bacterial extracts harboring the expressed E2 fusion protein molecules, 12 μg/ml of purified E1, 0.52 μg of $^{125}$I-ubiquitin, 1 unit of inorganic pyrophosphatase (pyrophosphate phosphohydrolase, EC 3.6.1.1) in 20 μl of 50 mM Tris (pH 7.6 at 25° C.), 10 mM $MgCl_2$, 1 mM ATP, 0.1 mM dithiothreitol and varying concentrations of the substrate. Prior to performing these conjugation assays, the activity of each E2 fusion molecule was determined by its ability to accept activated ubiquitin from E1 alone and bind to the ubiquitin via a thiol-ester bond by the method described in Sullivan and Vierstra, (1991) supra. Based on this thiol-ester assay, the volume of bacterial extracts that contained equivalent amounts of E2 activity was determined for each construction. This normalized volume was added to the various conjugation assays. The conjugation assays were terminated by adding an equal volume of 25 mM Tris-HCl (pH 6.8), 5% (v/v) glycerol, 4% (w/v) sodium dodecyl sulfate, 10% (v/v) 2-mercaptoethanol to the reactions and heating the mixture to 100° C. for 5 minutes. Samples were subjected to SDS-PAGE using the system of Laemmli, *Nature,* 227:680 (1970). The gels were then stained with Coomassie Blue, dried between sheets of cellophane, and used for autoradiography. This is intended to visualize the size of any proteins which have bound the radiolabeled ubiquitin to thus indicate if the radiolabeled ubiquitin molecule has been properly attached to the target protein of the expected size.

B. Conjugation of ubiquitin to immunoglobulins in the presence of eukaryotic extracts.

The formation of ubiquitin-antibody conjugates in the presence of wheat germ extracts or rabbit reticulocyte lysates were as described by Hatfield and Vierstra (1989), supra, for wheat germ. The reaction mixtures for these reactions were 20 μl total, containing 12 μg/ml of purified wheat E1, 50 μg/ml of human ubiquitin, 100 μg/ml of anti-S3 mono-clonal antibody, 30 units/ml of creatine kinase, and 4 μl of wheat germ extract or rabbit reticulocyte lysate (Promega) in 80 mM Tris (pH 8.5 at 25° C.), 20 mM creatine phosphate, 7.5 mM $MgCl_2$, 2 mM ATP, and 2 mM dithiothreitol. Each of the reactions was initiated by adding 2 μl of E2 fusion protein extracts and incubated at 30° C. for the indicated time periods. The reactions were terminated in the same manner as the expression conjugation assays described above. The samples were subjected to SDS-PAGE and the proteins were electroblotted to Immobilon-P. The antibody-conjugates were identified by immunoblot analysis using alkaline phosphatase-conjugated goat-anti-mouse immunoglobulins as described previously in Sullivan and Vierstra, supra.

C. Results of Conjugation Assays.

It was determined that in all cases *E. coli* was capable of expressing the chimeric UBC1 and UBC4 genes and to synthesize the synthetic E2 fusion proteins of the expected and desired sizes. All of E2 fusion proteins thus created were enzymatically active, based on their ability to interact with ubiquitin via the formation of a thiol ester bond to ubiquitin. When unmodified UBC1 or UBC4 was tested in ubiquitin conjugation assays, little or no conjugation was observed to the desired substrate tested. Conversely, when the appropriate fusions were tested, highly specific conjugation to the various substrates was observed, as demonstrated by appropriately sized bands on the radiolabeled blots indicating that proteins of the expected size were tagged with the radiolabeled ubiquitin. Thus the conjugation was detected by the attachment of free $^{125}$I-labeled ubiquitin to the target via a peptide bond. The formation of such ubiquitin-protein conjugates was visualized by the autoradiography as a mobility shift during the SDS-page analysis of ubiquitin from that of the free form to that of a protein expected to contain both ubiquitin and a substrate protein.

As an example, whereas UBC4 could not conjugate ubiquitin to the c-myc monoclonal antibody, the fusion protein expressed by the plasmid pET-UBC4-(c-myc) (FIG. 3) could in fact conjugate ubiquitin to the c-myc monoclonal antibody. In this particular experiment, a single ubiquitin was added to the heavy chain of the antibody. The ubiquitin-antibody conjugate migrated at the expected molecular mass of the heavy chain of the antibody (55 kDa) with the addition of a single ubiquitin moiety (6 kDa). The presence of the antibody in the conjugate was confirmed by its immunorecognition by Protein A. The reaction was judged to be specific for the c-myc antibody based on the fact that other mouse monoclonal antibodies failed to be conjugated by the E2 fusion protein expressed by the pET-UBC4-(c-myc) vector and also by the fact that addition of excess c-myc peptide blocked the antibody conjugation reaction.

Using the UBC1 E2 variant in which the c-myc epitope was fused directly to the UBC1 core region, attempts to perform similar experiments to add an ubiquitin conjugate to an antibody failed. Other experiments had hinted that perhaps a spacer arm, already present in UBC4, was required. Accordingly, the construct described above designated pET-UBC1-spacer-(c-myc) was constructed to test whether an artificial spacer arm would suffice to render the UBC1 fusion active. When the fusion protein expressed by the pET-UBC1-spacer-(c-myc) expression cassette was tested, it was found capable of specifically conjugating the radiolabeled ubiquitin to the c-myc monoclonal antibody. This result demonstrated that the protein binding ligand on the fusion protein which is specific to the target protein must be physically placed beyond the body of the E2 core region in such a fusion protein. As with UBC4-(c-myc), ubiquitin conjugated by the fusion protein including UBC1-spacer-(c-myc) was specific for the c-myc antibody, and it did not modify other mouse monoclonal antibodies. The fusion protein was also blocked by the addition of excess free-c-myc peptide to the reaction mixture.

To further test the ability of the system to conjugate ubiquitin to monoclonal antibodies, the construct including the domain D from Protein A was also tested. The E2 fusion protein created by the plasmid designated pET-UBC4-Protein A was added to conjugation reactions containing purified antibodies that naturally interact with Protein A. In these reactions, attachment of the ubiquitin moiety to the heavy chain of the antibodies was observed. In contrast, no such conjugation was observed when wild-type UBC4 was used in similar reactions. The ability to attached ubiquitin to the antibody correlated with the known affinity of Protein A to the various antibody classes. For example, whereas mouse immunoglobulin G, which binds to Protein A tightly, was quite effectively conjugated by the E2 fusion protein containing UBC4 and Protein A, an immunoglobulin G from goat, which normally binds weakly if at all to Protein A, was not similarly conjugated. Again the results were determined by radiolabeled blotting.

The interaction of the GeneV protein, which associates with itself into homodimers, which homodimers in turn bind cooperatively with single-stranded DNA, was also tested utilizing the UBC4-GeneV construct. First it was determined that a construct expressing the UBC4 protein itself was unable to conjugate ubiquitin to GeneV protein. Similar experiments were performed using the E2 fusion protein created by the plasmid pET-UBC4-GeneV. That fusion protein was found capable of creating ubiquitin-GeneV conjugates. In this case, the recognition of GeneV is apparently accomplished by the dimerization between the wild-type GeneV and the GeneV domain of the E2 fusion protein consisting of both UBC4 and GeneV. This demonstrates that dimerization-type affinities between the protein binding domain of the E2 fusion molecules constructed in accordance with the present invention will sufficiently bind to target proteins so as to allow them to be the target for ubiquitin fusion.

To test the ability of the E2 fusion protein strategy described herein to conjugate ubiquitin to hormones or receptors, the E2 fusion protein consisting of UBC4 and TGFα was utilized. Both TGFα and the related peptide hormone, epidermal growth factor, are capable of highly specific and very tight binding to the EGF receptor. When the E2 fusion protein expressed by the plasmid pET-UBC4-TGFα was added to crude human epidermal membranes, the result was highly specific modification of the EGFR protein by conjugation with ubiquitin. This conjugation was specific for the TGFα-EGFR pair as judged by the failure of unmodified UBC4 protein to ubiquitinate the receptor and the ability of free, excess, epidermal growth factor in the reaction mixture to block the reaction and prevent ubiquitination of the EGF receptor. The result also clearly demonstrates that species differentiations between E2s and ubiquitins are not critical to this reaction since the UBC4 plant origin is quite clearly capable of ubiquitinating the target molecule of mammalian origin in this reaction. Since M13 is a bacteriophage, the same phenomenon can be used on bacterial targets as well.

It is has been observed that selective proteolytic degradation by the ubiquitin-directed protein degradation pathway appears to involve the conjugation of multiple ubiquitins to the target protein, in many cases forming a multiubiquitin chain. In the conjugation assays described above, using the bacterial-expressed E2s, generally only attachment of a single ubiquitin to the target molecule was detected in most cases. As a result, it was possible to assert that ubiquitination by the E2 carboxyl-terminal fusion proteins described herein would not form the multiubiquitinated intermediates necessary to cause the targeted protein to enter into the degradative pathway.

To test whether that limitation was a real one, experiments were conducted in which crude eukaryotic cell extracts, either rabbit reticulocyte extract or wheat germ extract, were added to the ubiquitin conjugation assays. Since such crude extracts often contain endogenous multiubiquitin chains, the idea was to test to see of such multiubiquitin chains could be added by the E2 fusion proteins described herein to the target molecule. Such attachment of multiubiquitin chains to the target molecules was observed. For example, in the absence of such extracts, only a single ubiquitin becomes attached to mouse immunoglobulin G in the presence of E2 fusion protein consisting of UBC4-Protein A. But upon the addition of either wheat germ extract or rabbit reticulocyte extracts to the reaction mixture, the same system was capable of generating ubiquitinated forms of mouse immunoglobulin G with as many as 7-8 ubiquitin repeats attached to the antibody. Based on available evidence to date, such heavily modified forms represent acceptable substrates for subsequent degradation by the ubiquitin system and are highly likely to be recognized by that system and then subjected to proteolytic degradation. This results demonstrate that the E2 fusion proteins described herein are capable of generating proteolytic intermediates with the help of other endogenous factors normally present within eukaryotic cells.

Hypothetical Example

Figure 7:
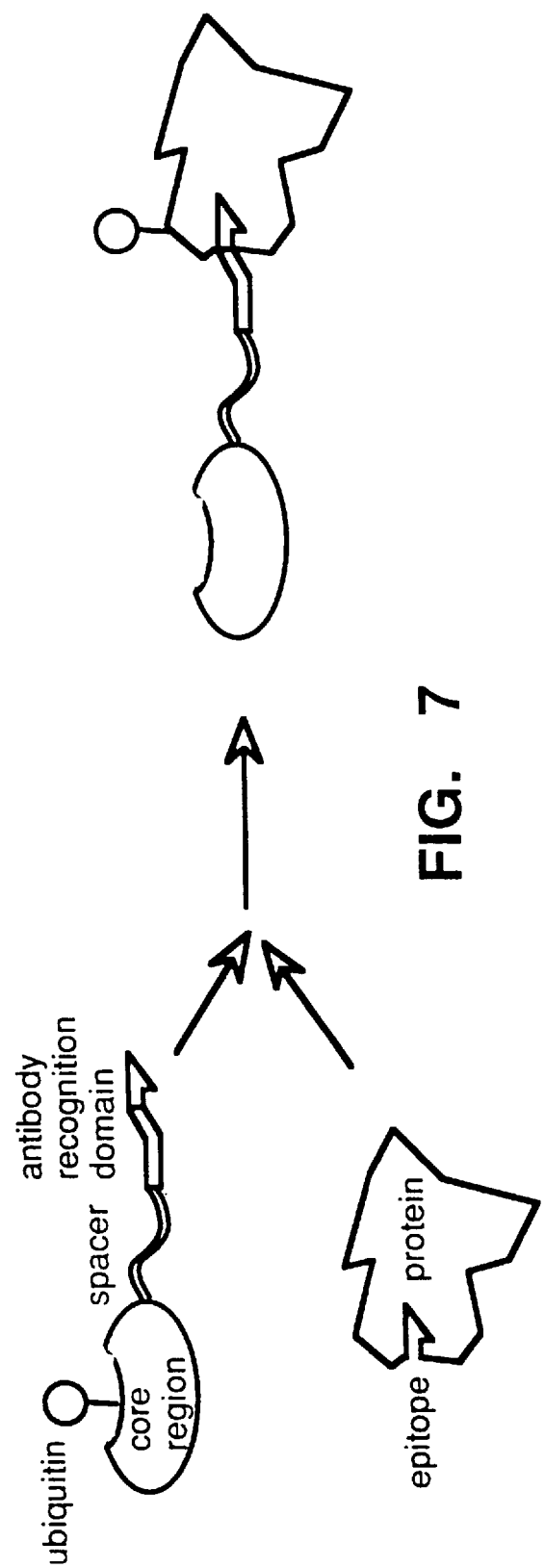

The experiments above demonstrate that the specificity of the ubiquitin conjugation can be modified in predetermined ways to target new proteins for degradation. The versatility of this approach depends on identifying a protein binding domain which can be attached to the E2 fusion molecule which will then bind to the protein of interest. Obviously, because the information is limited as to the nature of the interaction between many proteins and other proteins within the cell, the use of natural protein-protein interactions would restrict the technology present to only a few well characterized types. However, the exploitation of antibody/antigen reactions has the power to overcome this obstacle. It is possible, of course, to create antibodies which bind for most specific proteins of interest. The binding domains (Fab) of such antibodies, which involve amino acids from both the heavy and light immunoglobulin chains, can now be identified and expressed as single shorter peptides which are referred to as single chain monoclonal antibodies. The genes for the single chain monoclonal antibodies express Fab region fragments linked by a shorter flexible spacer region. This concept is illustrated in FIG. 7. It is intended that such single chain monoclonal antibodies can be fused to the carboxyl terminus of E2s like UBC4, to create E2 fusion proteins which can be targeted through the Fab region to any protein of interest for which a monoclonal antibody is either available or can be developed. There has recently been commercialized a kit for constructing this type of antibody which allows the facile development of single chain antibodies genes against any suitable antigenic protein. The availability of this technology suggests that E2 fusion proteins with an Fab protein ligand binding region can be constructed to target virtually any proteins for degradation using this system.

We claim:

1. A DNA sequence encoding an E2 fusion protein, the DNA sequence comprising:
    a promoter effective in the cells of a host to express a protein coding sequence located 3' to the promoter; and
    a DNA sequence encoding a fusion protein, the DNA fusion protein coding sequence located 3' to the promoter, the DNA sequence encoding the fusion protein including, 5' to 3':
    a DNA sequence encoding an E2 core region;
    a DNA sequence encoding a spacer of at least four amino acids; and
    a DNA sequence encoding a protein binding ligand having affinity for a target protein, the protein binding ligand not natively associated with any E2 protein, wherein
    the fusion protein encoded by the DNA sequence is capable of conjugating a ubiquitin moeity to proteins recognized by the protein binding ligand even in the ubiquitin protein ligase absence of an (E3).

2. A DNA sequence as claimed in claim 1 wherein protein binding ligand is a recognition domain of an antibody, the domain having binding specificity for the target protein.

3. A DNA sequence as claimed in claim 1 wherein the E2 core region is from a plant E2.

4. A DNA sequence as claimed in claim 1 wherein the E2 core region is selected from the group consisting of the core regions of UBC1, found in SEQ ID:NO:1 and UBC4, found in SEQ:ID:NO:3.

5. A DNA sequence as claimed in claim 1 wherein the DNA coding sequences for both the core region and the spacer are from a single native E2 coding region.

6. A DNA sequence as claimed in claim 1 wherein the DNA coding sequences for both the core region and the spacer are from UBC4, found in SEQ:ID:NO:3.

7. A DNA sequence as claimed in claim 1 wherein the spacer is an artificial amino acid sequence.

8. A DNA sequence as claimed in claim 1 wherein the protein binding ligand is a protein A domain having binding specificity for antibodies.

9. A DNA sequence as claimed in claim 1 wherein the protein binding ligand is selected from the group consisting of protein hormones and cellular receptors for protein hormones.

10. A DNA sequence as claimed in claim 1 wherein the protein binding ligand is an epitope recognized by an antibody.

11. A method of conjugating a ubiquitin moiety to a target protein comprising the steps of
(a) constructing a DNA sequence for an E2 fusion protein including:
a promoter effective in the cells of a host to express a protein coding sequence located 3' to the promoter; and
a DNA sequence encoding an E2 fusion protein, the DNA sequence located 3' to the promoter, the DNA sequence encoding the fusion protein including, 5' to 3':
a DNA sequence encoding an E2 core region;
a DNA sequence encoding a spacer of at least four amino acids; and
a DNA sequence encoding a protein binding ligand having affinity for the target protein, the protein binding ligand not natively associated with any E2 protein;
(b) transforming the DNA sequence from step (a) into a host in which the promoter is capable of causing expression of the E2 fusion protein, so that the E2 fusion protein is produced in the host; and
(c) exposing the E2 fusion protein to ubiquitin-linked E1, and a cellular source of energy so that the E2 fusion protein will accept the ubiquitin from the E1 and transfer the ubiquitin specifically to the target protein even in the absence of E3.

12. A method as claimed in claim 11 wherein the target protein is not in the host from step (b) and wherein the method further comprises the steps of recovering the E2 fusion protein expressed in the host and introducing the E2 fusion protein into a host in which the target protein is present.

13. A DNA sequence encoding an E2 fusion protein, the DNA sequence comprising:
a promoter effective in the cells of a host to express a protein coding sequence located 3' to the promoter; and
a DNA sequence encoding a fusion protein located 3' to the promoter, the DNA sequence encoding fusion protein including, 5' to 3':
a DNA sequence encoding an E2 core region;
a DNA sequence encoding a spacer of at least four amino acids; and
a DNA sequence encoding a protein binding ligand having affinity for a target protein, the protein binding ligand not natively associated with any E2 protein, the protein binding ligand being protein A wherein the fusion protein encoded by the fusion protein coding sequence is capable of conjugating a ubiquitin moeity to proteins to which protein A binds even in the absence of E3.

* * * * *

UNITED STATES PATENT AND TRADEMARK OFFICE
CERTIFICATE OF CORRECTION

PATENT NO. : 5,851,791
DATED : Dec. 22, 1998
INVENTOR(S) : Richard David Vierstra, et al It is certified that error appears in the above-identified patent and that said Letters Patent is hereby corrected as shown below:

Column 1, line 3
          add the following paragraph regarding federal funding:

This invention was made with United States government support awarded by the following agencies:

USDA NRI C6P (91-37301-6290)

The United States has certain rights in this invention.

Signed and Sealed this

Tenth Day of August, 1999

*Attest:*

Q. TODD DICKINSON

*Attesting Officer*    *Acting Commissioner of Patents and Trademarks*

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 757 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Arabidopsis thaliana ( i x ) FEATURE:
        ( A ) NAME/KEY: CDS
        ( B ) LOCATION: 100..558

( x ) PUBLICATION INFORMATION:
        ( A ) AUTHORS: Sullivan, M L
                      Vierstra, R D
        ( C ) JOURNAL: J. Biol. Chem.
        ( D ) VOLUME: 266
        ( F ) PAGES: 23878-23885
        ( G ) DATE: 1991

( x i ) SEQUENCE DESCRIPTION: SEQ ID NO:1:

```
CGGCGGTCAA  CACCGCTGAA  CACATATGAA  AGAAAGACGA  CCTCTTCTCT  CCGCGATCTT        60

TACCTCAACA  ACGAGATCTG  TTTCCAGAAA  GAAAGGAGG  ATG TCG ACG CCA GCA           114
                                               Met Ser Thr Pro Ala
                                                 1               5

AGG AAG AGG TTA ATG AGG GAT TTC AAG AGG TTG CAG CAA GAC CCA CCT              162
Arg Lys Arg Leu Met Arg Asp Phe Lys Arg Leu Gln Gln Asp Pro Pro
             10                  15                  20

GCG GGT ATT AGT GGT GCT CCA CAG GAC AAC AAC ATT ATG CTC TGG AAT              210
Ala Gly Ile Ser Gly Ala Pro Gln Asp Asn Asn Ile Met Leu Trp Asn
             25                  30                  35

GCT GTC ATA TTT GGG CCT GAT GAC ACA CCA TGG GAT GGA GGT ACT TTC              258
Ala Val Ile Phe Gly Pro Asp Asp Thr Pro Trp Asp Gly Gly Thr Phe
             40                  45                  50

AAA CTC TCA CTG CAG TTC TCT GAA GAT TAT CCC AAT AAA CCA CCA ACA              306
Lys Leu Ser Leu Gln Phe Ser Glu Asp Tyr Pro Asn Lys Pro Pro Thr
         55                  60                  65

GTT CGG TTT GTG TCA CGG ATG TTT CAT CCT AAT ATT TAT GCA GAT GGG              354
Val Arg Phe Val Ser Arg Met Phe His Pro Asn Ile Tyr Ala Asp Gly
 70                  75                  80                  85

AGT ATC TGC TTG GAC ATT CTA CAA AAC CAG TGG AGT CCA ATC TAT GAT              402
Ser Ile Cys Leu Asp Ile Leu Gln Asn Gln Trp Ser Pro Ile Tyr Asp
                 90                  95                 100

GTT GCT GCT ATA CTT ACC TCC ATC CAG TCC TTG CTC TGT GAC CCT AAT              450
Val Ala Ala Ile Leu Thr Ser Ile Gln Ser Leu Leu Cys Asp Pro Asn
                105                 110                 115

CCG AAT TCT CCT GCA AAC TCG GAA GCT GCT CGG ATG TAC AGC GAA AGC              498
Pro Asn Ser Pro Ala Asn Ser Glu Ala Ala Arg Met Tyr Ser Glu Ser
            120                 125                 130

AAG CGC GAG TAC AAC AGG AGA GTG CGT GAT GTT GTT GAG CAA AGC TGG              546
Lys Arg Glu Tyr Asn Arg Arg Val Arg Asp Val Val Glu Gln Ser Trp
        135                 140                 145

ACT GCT GAC TAGTAGTAGT TTGTTGTAAG CGTTGTAGCT CTCTCTACTT                       595
Thr Ala Asp
150

TCTCTCAATC  ACGATTCAGC  AACAGCTTTC  TTCTCTTTTC  ATTCATGTCT  TGTGTTTCCA        655

AAACTATTTA  AGTGATTCCA  TGCTTTGATG  TAACCCAACA  TCCTAAAAAA  AACAACTTTG        715

TACCAAACCA  TCTGAATTAT  TCACTTTTGT  GTATAAAAAA  AA                           757
```

( 2 ) INFORMATION FOR SEQ ID NO:2:

( i ) SEQUENCE CHARACTERISTICS:
        ( A ) LENGTH: 152 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ser Thr Pro Ala Arg Lys Arg Leu Met Arg Asp Phe Lys Arg Leu
 1               5                  10                 15
Gln Gln Asp Pro Pro Ala Gly Ile Ser Gly Ala Pro Gln Asp Asn Asn
                20                  25                 30
Ile Met Leu Trp Asn Ala Val Ile Phe Gly Pro Asp Asp Thr Pro Trp
             35                  40                 45
Asp Gly Gly Thr Phe Lys Leu Ser Leu Gln Phe Ser Glu Asp Tyr Pro
         50                  55                 60
Asn Lys Pro Pro Thr Val Arg Phe Val Ser Arg Met Phe His Pro Asn
 65                  70                  75                 80
Ile Tyr Ala Asp Gly Ser Ile Cys Leu Asp Ile Leu Gln Asn Gln Trp
                 85                  90                 95
Ser Pro Ile Tyr Asp Val Ala Ala Ile Leu Thr Ser Ile Gln Ser Leu
                100                 105                110
Leu Cys Asp Pro Asn Pro Asn Ser Pro Ala Asn Ser Glu Ala Ala Arg
            115                 120                 125
Met Tyr Ser Glu Ser Lys Arg Glu Tyr Asn Arg Arg Val Arg Asp Val
        130                 135                 140
Val Glu Gln Ser Trp Thr Ala Asp
145                 150
```

( 2 ) INFORMATION FOR SEQ ID NO:3:

( i ) SEQUENCE CHARACTERISTICS:
        ( A ) LENGTH: 980 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Triticum vulgare ( i x ) FEATURE:
        ( A ) NAME/KEY: CDS
        ( B ) LOCATION: 60..614

( x ) PUBLICATION INFORMATION:
        ( A ) AUTHORS: Sullivan, M L
                     Vierstra, R D
        ( C ) JOURNAL: Proc. Natl. Acad. Sci. U.S.A.
        ( D ) VOLUME: 86
        ( F ) PAGES: 9861-9865
        ( G ) DATE: 1989

( x i ) SEQUENCE DESCRIPTION: SEQ ID NO:3:

```
GGAATTCCCA AACCTACAAG CAGGGCAAGG AGGAGGAGGA AGAAGAAGAA GAAGCAAAC            59

ATG TCT TCC CCA AGC AAG CGC AGG GAG ATG GAT CTC ATG AAG CTG ATG           107
Met Ser Ser Pro Ser Lys Arg Arg Glu Met Asp Leu Met Lys Leu Met
 1               5                  10                 15

ATG AGT GAC TAC AAG GTG GAC ATG ATC AAC GAC GGG ATG CAC GAG TTC           155
Met Ser Asp Tyr Lys Val Asp Met Ile Asn Asp Gly Met His Glu Phe
                20                  25                 30
```

```
TTC GTC CAC TTC CAC GGA CCC AAA GAC AGT ATT TAC CAG GGT GGT GTG      203
Phe Val His Phe His Gly Pro Lys Asp Ser Ile Tyr Gln Gly Gly Val
         35                      40                  45

TGG AAG GTC AGG GTT GAA CTC ACC GAA GCT TAC CCT TAC AAA TCC CCT      251
Trp Lys Val Arg Val Glu Leu Thr Glu Ala Tyr Pro Tyr Lys Ser Pro
     50                      55                  60

TCC ATT GGC TTC ACC AAC AAG ATC TAT CAC CCC AAT GTC GAT GAG ATG      299
Ser Ile Gly Phe Thr Asn Lys Ile Tyr His Pro Asn Val Asp Glu Met
 65                      70                  75                  80

TCT GGT TCT GTC TGC TTG GAT GTG ATC AAT CAG ACA TGG AGC CCG ATG      347
Ser Gly Ser Val Cys Leu Asp Val Ile Asn Gln Thr Trp Ser Pro Met
                 85                      90                  95

TTT GAC CTT GTG AAT ATC TTT GAG GTG TTC CTG CCC CAG CTT CTC CTG      395
Phe Asp Leu Val Asn Ile Phe Glu Val Phe Leu Pro Gln Leu Leu Leu
                100                     105                 110

TAC CCG AAC CCC TCG GAC CCC TTG AAC GGC GAG GCG GCT TCG CTC ATG      443
Tyr Pro Asn Pro Ser Asp Pro Leu Asn Gly Glu Ala Ala Ser Leu Met
             115                     120                 125

ATG CGC GAC AAG AAT GCC TAT GAA AAT AAA GTC AAA GAA TAT TGT GAG      491
Met Arg Asp Lys Asn Ala Tyr Glu Asn Lys Val Lys Glu Tyr Cys Glu
         130                     135                 140

AGA TAT GCC AAG CCT GAA GAT ATA TCC CCA GAG GAG GAA GAG GAG GAG      539
Arg Tyr Ala Lys Pro Glu Asp Ile Ser Pro Glu Glu Glu Glu Glu Glu
145                     150                 155                 160

AGT GAT GAG GAG CTG AGC GAC GCC GAG GGC TAC GAC TCC GGC GAC GAG      587
Ser Asp Glu Glu Leu Ser Asp Ala Glu Gly Tyr Asp Ser Gly Asp Glu
                 165                     170                 175

GCC ATC ATG GGC CAC GCA GAC CCT        TAACTGGTGG ATGGATGCAA GGATGGTTAG    641
Ala Ile Met Gly His Ala Asp Pro
             180                     185

CTCAGTCAGT AACTCAGTAA TGCAGGTGAT CATGATGTAT CTCTGTCTGT CAGTCTGTAC    701

ATAGCTGCGG CGATCACTGA TGAATGCCGC CATGGCAGAT GCTGAAGAAA GTCATCAGCC    761

ATCTCAACTC AGCTCCACTA GTTCTTGTGT GTCCCGCTGT GAATAACTTG CCATTTGTTT    821

GTGTTGGTTC CATTTGCAGT TCATGTTTCC ATTCTAGGAG ATGTCTGTTC TTCTGTTTTG    881

TTGATTTCAT TTCCAGTTCA TGTTACTACT GTATGTTTCC CTTTCCTACC TGTAATCATC    941

TCAGGGGAAT TTAAATCTGC TCTGCATGTC CAGGAATTC                           980
```

( 2 ) INFORMATION FOR SEQ ID NO:4:

( i ) SEQUENCE CHARACTERISTICS:
        ( A ) LENGTH: 184 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ser Ser Pro Ser Lys Arg Arg Glu Met Asp Leu Met Lys Leu Met
 1               5                  10                  15

Met Ser Asp Tyr Lys Val Asp Met Ile Asn Asp Gly Met His Glu Phe
             20                  25                  30

Phe Val His Phe His Gly Pro Lys Asp Ser Ile Tyr Gln Gly Gly Val
         35                  40                  45

Trp Lys Val Arg Val Glu Leu Thr Glu Ala Tyr Pro Tyr Lys Ser Pro
     50                  55                  60

Ser Ile Gly Phe Thr Asn Lys Ile Tyr His Pro Asn Val Asp Glu Met
 65                  70                  75                  80
```

```
Ser  Gly  Ser  Val  Cys  Leu  Asp  Val  Ile  Asn  Gln  Thr  Trp  Ser  Pro  Met
               85                      90                           95

Phe  Asp  Leu  Val  Asn  Ile  Phe  Glu  Val  Phe  Leu  Pro  Gln  Leu  Leu  Leu
              100                     105                      110

Tyr  Pro  Asn  Pro  Ser  Asp  Pro  Leu  Asn  Gly  Glu  Ala  Ala  Ser  Leu  Met
              115                     120                     125

Met  Arg  Asp  Lys  Asn  Ala  Tyr  Glu  Asn  Lys  Val  Lys  Glu  Tyr  Cys  Glu
     130                     135                     140

Arg  Tyr  Ala  Lys  Pro  Glu  Asp  Ile  Ser  Pro  Glu  Glu  Glu  Glu  Glu  Glu
145                      150                     155                          160

Ser  Asp  Glu  Glu  Leu  Ser  Asp  Ala  Glu  Gly  Tyr  Asp  Ser  Gly  Asp  Glu
               165                     170                      175

Ala  Ile  Met  Gly  His  Ala  Asp  Pro
               180
```

(2) INFORMATION FOR SEQ ID NO:5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:5:

GGCCACGCAG ACCCTCTCGA GTAGGATGGA TGCAAGG       37

(2) INFORMATION FOR SEQ ID NO:6:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:6:

GCAAAGCTGG ACTGCTCTCG AGTAGTAGTT TGTTGTAAGC G       41

(2) INFORMATION FOR SEQ ID NO:7:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 6..35

(xi) SEQUENCE DESCRIPTION: SEQ ID NO:7:

```
TCGAG GAG CAG AAG CTG ATC AGC GAG GAG GAC CTG TAAC        39
      Glu Gln Lys Leu Ile Ser Glu Glu Asp Leu
       1           5                   10
```

(2) INFORMATION FOR SEQ ID NO:8:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:8:

```
Glu Gln Lys Leu Ile Ser Glu Glu Asp Leu
 1           5                   10
```

( 2 ) INFORMATION FOR SEQ ID NO:9:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TCGAGTTACA GGTCCTCCTC GCTGATCAGC TTCTGCTCC     39

( 2 ) INFORMATION FOR SEQ ID NO:10:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CCCGCCCGTG GCTGCACTCG AGGTGTCCCA TTTTAATGAC TGCCC     45

( 2 ) INFORMATION FOR SEQ ID NO:11:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GGCCTGCTTC TTCTGGCTGG CGTCGACCTA GGCCAGGAGG TCCGCATGC     49

( 2 ) INFORMATION FOR SEQ ID NO:12:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

AGGTAACTCG AGATGATTAA AGTTGAAATT AAACC     35

( 2 ) INFORMATION FOR SEQ ID NO:13:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

CGACCTGGTC GACGTTACTT AGCCGGAACG AGGC     34

( 2 ) INFORMATION FOR SEQ ID NO:14:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

CTTAATGACC TCGAGGCTCC AAAAGCTGAT GCGCAAC     37

( 2 ) INFORMATION FOR SEQ ID NO:15:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
GTTGAAATTC  TCGAGTTATT  TCGGTGCTTG  AGATTCG                         37
```

( 2 ) INFORMATION FOR SEQ ID NO:16:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 3..32

( x i ) SEQUENCE DESCRIPTION: SEQ ID NO:16:

```
TC  GAA  CCA  CCA  GTC  GAC  GCA  GCA  GCA  GCA  GCA  CTCGAGT       39
    Glu  Pro  Pro  Val  Asp  Ala  Ala  Ala  Ala  Ala
    1                  5                        10
```

( 2 ) INFORMATION FOR SEQ ID NO:17:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Glu  Pro  Pro  Val  Asp  Ala  Ala  Ala  Ala  Ala
1                  5                        10
```

( 2 ) INFORMATION FOR SEQ ID NO:18:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
TCGAACTCGA  GTGCTGCTGC  TGCTGCGTCG  ACTGGTGGT                       39
```